United States Patent [19]
Dupuis et al.

[11] Patent Number: 6,120,780
[45] Date of Patent: *Sep. 19, 2000

[54] COSMETIC USE OF A CROSSLINKED AND AT LEAST 90% NEUTRALIZED POLY(2-ACRYLAMIDO-2-METHYLPROPANESULPHONIC ACID) AND TOPICAL COMPOSITIONS CONTAINING IT

[75] Inventors: Christine Dupuis; Isabelle Hansenne, both of Paris; Mireille Maubru, Chatou; Laurence Sebillotte-Arnaud, L'Hay les Roses; Raluca Lorant, Thiais, all of France

[73] Assignee: L'Oreal, Paris, France

[ * ] Notice: This patent is subject to a terminal disclaimer.

[21] Appl. No.: 09/029,514

[22] PCT Filed: Jun. 18, 1997

[86] PCT No.: PCT/FR97/01098

§ 371 Date: Oct. 27, 1998

§ 102(e) Date: Oct. 27, 1998

[87] PCT Pub. No.: WO98/00094

PCT Pub. Date: Jan. 8, 1998

[30] Foreign Application Priority Data

Jun. 28, 1996 [FR] France .................................. 96 08107

[51] Int. Cl.$^7$ ...................................................... A61K 7/48
[52] U.S. Cl. .............................. 424/401; 424/59; 424/61; 424/70.1; 424/70.5; 424/70.7; 514/844; 514/845; 514/937; 514/944
[58] Field of Search ................................... 424/401, 70.1, 424/70.5, 70.7, 59, 61; 514/844, 845, 937, 944

[56] References Cited

U.S. PATENT DOCUMENTS 5,034,218 7/1991 Duvel .
5,114,706 5/1992 Duvel .
5,368,850 11/1994 Cauwet et al. .......................... 424/70.1
5,470,551 11/1995 Dubief et al. ..
5,879,718 3/1999 Sebillote-Arnaud .................... 424/70.5
5,891,452 4/1999 Sebillote-Arnaud et al. .......... 424/401

*Primary Examiner*—Jyothsan Venkat
*Attorney, Agent, or Firm*—Finnegan, Henderson, Farabow, Garrett & Dunner, L.L.P.

[57] ABSTRACT

The present application relates to the use, as a cosmetic product, of crosslinked and at least 90% neutralized poly (2-acrylamido-2-methylpropanesulphonic acid) polymers. They generally comprise, distributed randomly:
a) from 90 to 99.9% by weight of units of general formula (1) below:

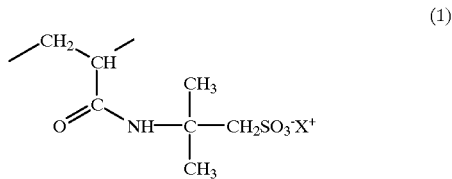

(1)

in which $X^+$ denotes a cation or a mixture of cations, not more than 10 mol % of the cations $X^+$ being able to be protons $H^+$;

b) from 0.01 to 10% by weight of crosslinking units derived from at least one monomer having at least two olefinic double bonds; the weight proportions being defined relative to the total weight of the polymer.

The present application relates in particular to their use as thickener and/or gelling agent in cosmetic and/or dermatological compositions.

30 Claims, No Drawings

COSMETIC USE OF A CROSSLINKED AND AT LEAST 90% NEUTRALIZED POLY(2-ACRYLAMIDO-2-METHYLPROPANESULPHONIC ACID) AND TOPICAL COMPOSITIONS CONTAINING IT

This application is 371 of PCT/FR97/01098 filed Jun. 18, 1997.

The present application relates to the use, as a cosmetic product, of crosslinked, at least 90% neutralized, poly(2-acrylamido-2-methylpropanesulphonic acid) polymers and to cosmetic or dermatological compositions containing them.

Cosmetic or dermatological compositions generally have a high viscosity and are mostly formulated in a thickened liquid form such as a milk, a cream, a gel or a paste. This type of presentation is greatly favoured by consumers; it is usually an issue which is a practical preoccupation for the formulator: facilitating the removal of the product from its packaging without any significant loss, limiting the diffusion of the product to the local area of treatment and being able to use it in sufficient amounts to obtain the desired cosmetic or dermatological effect.

This objective is important for formulations such as those of make-up, hygiene or care products which should spread well, homogeneously over the local surface to be treated, as well as hair compositions, which should spread well and distribute themselves uniformly along the keratin fibres and should not run down the forehead, the nape of the neck or the face or into the eyes.

In order to satisfy these conditions, the viscosity of the compositions is increased by adding thickening and/or gelling polymers.

Poly(2-acrylamido-2-methylpropanesulphonic acid) homopolymers such as the commercial products Cosmedia HSP1160 and Rheotik 8011 from the company Henkel are known in the prior art. They are used as thickeners and/or gelling agents in many cosmetic formulations. These polymers do not make it possible to obtain stable and homogeneous compositions which can reach high viscosities over a wide pH range. They usually lead to heterogeneous, stringy and sticky fluid gels.

The applicant has discovered, surprisingly, a novel family of thickening and/or gelling polymers which makes it possible to obtain a very large number of cosmetic and dermatological formulations which may contain supports of different nature.

The subject of the invention is the use, as cosmetic products, of crosslinked and at least 90% neutralized poly (2-acrylamido-2-methylpropanesulphonic acid) polymers which will be defined in greater detail in the rest of the description.

The invention relates, in particular, to their use as thickeners and/or gelling agents in cosmetic and/or dermatological compositions.

These polymers make it possible in particular to prepare many aqueous compositions, over a wide pH range, the viscosity of which remains stable over time at room temperature or at higher temperatures.

They also make it possible to produce transparent, homogeneous, non-runny, non-stringy aqueous gels which are soft and slippery when applied and stable on storage.

The crosslinked and totally or almost totally neutralized poly(2-acrylamido-2-methylpropanesulphonic acid) polymers in accordance with the invention are water-soluble or swellable in water. They are generally characterized in that they comprise, distributed randomly:

a) from 90 to 99.9% by weight of units of general formula (1) below:

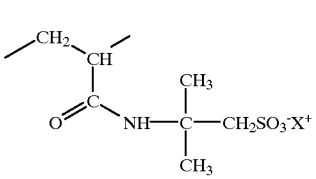

in which $X^+$ denotes a cation or a mixture of cations, not more than 10 mol % of the cations $X^+$ being able to be protons $H^+$;

b) from 0.01 to 10% by weight of crosslinking units derived from at least one monomer having at least two olefinic double bonds; the weight proportions being defined relative to the total weight of the polymer.

Preferably, the polymers of the invention contain a number of units of formula (1) in an amount which is sufficiently high to obtain polymer particles whose hydrodynamic volume in solution in water has a radius ranging from 10 to 500 nm and whose distribution is homogeneous and unimodal.

The polymers according to the invention more particularly preferred comprise from 98 to 99.5% by weight of units of formula (1) and from 0.2 to 2% by weight of crosslinking units.

$X^+$ represents a cation or a mixture of cations chosen in particular from a proton, an alkali metal cation, a cation equivalent to that of an alkaline-earth metal or the ammonium ion.

More particularly, 90 to 100 mol % of the cations are $NH_4^+$ cations and 0 to 10 mol % are protons ($H^+$).

The crosslinking monomers having at least two olefinic double bonds are chosen, for example, from dipropylene glycol diallyl ether, polyglycol diallyl ethers, triethylene glycol divinyl ether, hydroquinone diallyl ether, tetrallyloxethanoyl or other polyfunctional allyl or vinyl ether alcohols, tetraethylene glycol diacrylate, triallylamine, trimethylolpropane diallyl ether, methylene bisacrylamide and divinylbenzene.

The crosslinking monomers having at least two olefinic double bonds are more particularly chosen from those corresponding to the general formula (2) below:

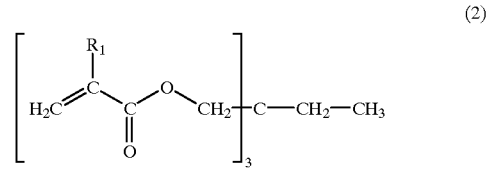

in which $R_1$ denotes a hydrogen atom or a $C_1$–$C_4$ alkyl and more particularly methyl (trimethylolpropane triacrylate).

The reaction for the polymerization of the polymers of the invention produces not only linear chains but also branched or crosslinked polymer molecules. These molecules may be characterized in particular by their rheological behaviour in water, but more particularly by dynamic light scattering.

In the case of characterization of the molecules by dynamic light scattering, the distribution of the hydrodynamic volume of the polymer structures is measured. The macromolecules dissolved in the water are flexible and surrounded by a salvation sheath formed of water molecules. With charged polymers such as those of the invention, the size of the molecules depends on the amount of salt in the water. In polar solvents, the uniform charge along the main chain of the polymer leads to a considerable expansion of the polymer chain. Increasing the amount of salt increases the amount of electrolyte in the solvent and separates the uniform charges of the polymer. In addition to the molecules transported in the salvation sheath, the solvent molecules are bound in the cavities of the polymer. In this case, the solvent molecules form part of the macromolecules in the solution and move at the same average speed. Thus, the hydrodynamic volume describes the linear dimension of the macromolecule and of these solvation molecules.

The hydrodynamic volume $v_h$ is determined by the following formula:

$$v_h = M/N_A \times (V_2 + dV_1)$$

with:

M denoting the mass in grams of the undissolved macromolecule;

$N_A$ denoting Avogadro's number;

$V_1$ denoting the specific volume of the solvent;

$V_2$ denoting the specific volume of the macromolecule;

d is the mass in grams of the solvent which is associated with 1 gram of undissolved macromolecule.

If the hydrodynamic particle is spherical, it is then easy to calculate the hydrodynamic radius from the hydrodynamic volume, by the formula:

$$v_h = 4\Pi R^3/3$$

with R denoting the dynamic radius.

The cases where the hydrodynamic particles are perfectly spherical are extremely rare. Most synthetic polymers involve highly eccentric ellipsoids or compacted structures. In this case, the radius is determined on a sphere which is equivalent, from a frictional point of view, to the shape of the particle in question.

As a general rule, the work is carried out on molecular weight distributions and thus on hydrodynamic volume and radius distributions. For polydispersed systems, the distribution of the coefficients of diffusion must be calculated. From this distribution, the results relating to the radial distribution and to the distribution of the hydrodynamic volumes are deduced.

The hydrodynamic volumes of the polymers of the invention are determined in particular by dynamic light scattering from the diffusion coefficients D according to the Stokes-Einstein formula: $D = kT/6\Pi\eta R$ where k is the Boltzmann constant, T is the absolute temperature in degrees Kelvin, 77 is the viscosity of the solvent (water) and R is the hydrodynamic radius.

These coefficients of diffusion D are measured according to the method of characterization of a mixture of polymers by laser diffusion described in the following references:

(1) Pecora, R; Dynamic Light Scattering; Plenium Press, New York, 1976;
(2) Chu, B; Dynamic Light Scattering; Academic Press, New York, 1994;
(3) Schmitz, K S; Introduction to Dynamic Light Scattering; Academic Press, New York, 1990;
(4) Provincher S. W.; Comp. Phys., 27,213, 1982;
(5) Provincher S. W.; Comp. Phys., 27,229, 1982;
(6) ALV Laservertriebgesellschaft mbH, Robert Bosch Str. 47, D-63225 Langen, Germany;
(7) ELS-Reinheimer Strasse 11, D-64846 Gross-Zimmern, Germany;
(8) CHI W U et al., Macromolecules, 1995, 28,4914–4919.

The polymers which are particularly preferred are those having a viscosity, measured with a Brookfield viscometer, rotor 4, at a spin speed of 100 revolutions/minute in an aqueous 2% solution and at 25° C., of greater than or equal to 1000 cps and more preferably ranging from 5000 to 40,000 cps and more particularly from 6500 to 35,000 cps.

The crosslinked poly(2-acrylamido-2methylpropanesulphonic acids) of the invention may be obtained according to the preparation process comprising the following steps:

(a) the 2-acrylamido-2-methylpropanesulphonic acid monomer is dispersed or dissolved in free form in a tert-butanol or water and tert-butanol solution;

(b) the monomer solution or dispersion obtained in (a) is neutralized with one or more inorganic or organic bases, preferably aqueous ammonia $NH_3$, in an amount which makes it possible to obtain a degree of neutralization of the sulphonic acid functions of the polymer ranging from 90 to 100%;

(c) the crosslinking monomer or monomers is (are) added to the solution or dispersion obtained in (b);

(d) a standard radical polymerization is carried out in the presence of free-radical initiators at a temperature ranging from 10 to 150° C., the polymer precipitating in the tert-butanol-based solution or dispersion.

Another subject of the invention consists of cosmetic or dermatological compositions containing, in a cosmetically acceptable medium, at least one crosslinked and at least 90% neutralized poly(2acylamido-2-methylpropanesulphonic acid) as described above.

The crosslinked, totally or almost totally neutralized poly(2-acrylamido-2-methylpropanesulphonic acids) are present in the cosmetic or dermatological compositions of the invention in concentrations preferably ranging from 0.01 to 20% by weight relative to the total weight of the composition and more preferably from 0.1 to 10% by weight.

The compositions of the invention contain a cosmetically or dermatologically acceptable medium, that is to say a medium that is compatible with any keratin substance, such as the skin, the nails, the mucous membranes and the hair, or any other area of body skin.

The compositions preferably contain a cosmetically and/or dermatologically acceptable aqueous medium. They have a pH which may range preferably from 1 to 13 and more preferably from 2 to 12.

The cosmetically and/or dermatologically acceptable medium of the compositions according to the invention more particularly consists of water and optionally of cosmetically and/or dermatologically acceptable organic solvents.

The organic solvents may represent from 5% to 98% of the total weight of the composition. They may be chosen from the group consisting of hydrophilic organic solvents, lipophilic organic solvents, amphiphilic solvents or mixtures thereof.

Among the hydrophilic organic solvents, mention may be made, for example, of linear or branched lower monoalcohols having from 1 to 8 carbon atoms, such as ethanol, propanol, butanol, isopropanol and isobutanol; polyethylene glycols having from 6 to 80 ethylene oxides; polyols such as propylene glycol, butylene glycol, glycerol and sorbitol; mono- or dialkyl isosorbide in which the alkyl groups have from 1 to 5 carbon atoms, such as dimethyl isosorbide; glycol ethers such as diethylene glycol monomethyl or monoethyl ether and propylene glycol ethers such as dipropylene glycol methyl ether.

As amphiphilic organic solvents, mention may be made of polyols such as polypropylene glycol (PPG) derivatives, such as fatty acid esters of polypropylene glycol and fatty alcohol ethers of PPG, for instance PPG-23 oleyl ether and PPG-36 oleate.

As lipophilic organic solvents, mention may be made, for example, of fatty esters such as diisopropyl adipate, dioctyl adipate and alkyl benzoates.

In order for the cosmetic or dermatological compositions of the invention to be more pleasant to use (softer on application, more nourishing and more emollient), it is possible to add a fatty phase to the medium of these compositions.

The fatty phase preferably represents from 0% to 50% of the total weight of the composition.

This fatty phase may contain one or more oils preferably chosen from the group consisting of:

water-soluble or liposoluble, organomodified or non-organomodified, linear, branched or cyclic, volatile or non-volatile silicones, mineral oils such as liquid paraffin and liquid petroleum jelly, oils of animal origin such as perhydrosqualene, oils of plant origin such as sweet almond oil, avocado oil, castor oil, olive oil, jojoba oil, sesame oil, groundnut oil, macadamia oil, grapeseed oil, rapeseed oil or coconut oil, synthetic oils such as purcellin oil and isoparaffins, fluorooils and perfluoro oils, fatty acid esters such as purcellin oil.

This phase may also contain as fatty substance one or more fatty alcohols, fatty acids, (stearic acid) or waxes (paraffin wax, polyethylene wax, carnauba wax or beeswax).

In a known manner, all the compositions of the invention may contain adjuvants that are common in the cosmetic and dermatological fields, other standard gelling agents and/or thickeners; polymers; emulsifiers; surfactants; moisturizers; emollients; sunscreens; hydrophilic or lipophilic active agents such as ceramides; anti-free-radical agents; insect repellents; slimming agents; bactericides; sequestering agents; antidandruff agents; antioxidants; preserving agents; basifying or acidifying agents; fragrances; fillers; dyestuffs. The amounts of these various adjuvants are those conventionally used in the fields in question.

Obviously, a person skilled in the art will take care to select the optional compound or compounds to be added to the composition according to the invention such that the advantageous properties intrinsically associated with the composition in accordance with the invention are not, or are not substantially, adversely affected by the addition envisaged.

The compositions according to the invention may be in any form which is suitable for topical application, in particular in the form of solutions of the lotion or serum type; in the form of aqueous gels; in the form of emulsions obtained by dispersing a fatty phase in an aqueous phase (O/W) or, conversely, (W/O), of liquid, semi-liquid or solid consistency such as milks, relatively smooth creams, or pastes. These compositions are prepared according to the usual methods.

The compositions according to the invention may be used as rinse-out hair products or as leave-in hair products, in particular for washing, care, conditioning or maintenance of the hairstyle or for shaping keratin fibres such as the hair.

They may be styling products such as hair setting lotions, blow-drying lotions and fixing and styling compositions. The lotions may be packaged in various forms, in particular in vaporizers, pump-dispenser bottles or in aerosol cans in order to apply the composition in vaporized form or in the form of a mousse. Such forms of packaging are indicated, for example, when it is desired to obtain a spray or a mousse for fixing or treating the hair. The compositions of the invention may also be shampoos or rinse-out or leave-in compositions to be applied before or after shampooing, dyeing, bleaching, permanent-waving or straightening the hair.

The compositions of the invention may also be used as hygiene and/or care products, such as protective, treatment or care creams for the face, for the hands or for the body, protective or care body milks, and lotions, gels or mousses to care for the skin or the mucous membranes or for cleansing the skin.

The compositions of the invention may also be used as antisun products.

The compositions may also consist of solid preparations constituting cleansing soaps or bars.

The compositions of the invention may also be used as buccodental care products, such as toothpastes and mouthwashes.

The compositions may be make-up products such as face creams, foundations, mascaras, eye-liners or lipsticks.

Another subject of the invention is a process for the non-therapeutic cosmetic treatment of the skin, the scalp, the hair, the eyelashes, the eyebrows, the nails or the mucous membranes, characterized in that a composition as defined above is applied to the keratin support according to the usual technique for using this composition. For example: application of creams, gels, sera, lotions or milks to the skin, the scalp and/or the mucous membranes.

The examples which follow illustrate the invention without being limiting in nature.

PREPARATION EXAMPLE A 2006.2 g of tert-butanol are introduced into a 5 liter round-bottomed flask fitted with a stirrer, a reflux condenser, a thermometer and a delivery-tube device for the nitrogen and the ammonia, followed by 340.0 g of 2-acrylamido-2-methylpropanesulphonic acid which is dispersed in the solvent with vigorous stirring. After 30 minutes, the ammonia is added via the upper delivery tube of the flask and the reaction medium is maintained at room temperature for 30 minutes until a pH of about 6–6.5 is obtained. 32.0 g of a 25% solution of trimethylolpropane triacrylate in tert-butanol are then introduced and the reaction medium is heated to 60° C. and simultaneously made inert by introducing nitrogen into the flask. Once this temperature has been reached, dilauroyl peroxide is added. The reaction starts immediately, which is reflected in an increase in temperature and a precipitation of the polymer. 15 minutes after the start of the polymerization, a stream of nitrogen is introduced. 30 minutes after adding the initiator, the temperature of the reaction medium reaches a maximum of 65–70° C. 30 minutes after this temperature has been reached, the medium is heated to reflux and is maintained under these conditions for 2 hours. The formation of a thick paste is observed in the course of the reaction. The mixture is cooled to room temperature and the product obtained is filtered off. The recovered paste is then dried under vacuum at 60–70° C. for 24 hours. 391 g of crosslinked and neutralized poly(2acrylamido-2-methylpropanesulphonic acid) are obtained, having a viscosity, measured with a Brookfield viscometer, rotor 4, at a spin speed of 100 revolutions/minute in an aqueous 2% solution and at 25° C., ranging from 15,000 cps to 35,000 cps. The viscosity of the polymer will be chosen and controlled according to standard means depending on the cosmetic application envisaged.

The hydrodynamic radius of the polymer obtained in an aqueous solution, determined by dynamic light scattering, is 440 nm.

PREPARATION EXAMPLE B 2006.2 g of tert-butanol are introduced into a 5 liter round-bottomed flask fitted with a stirrer, a reflux condenser, a thermometer and a delivery-tube device for the nitrogen and the ammonia, followed by 340.0 g of 2-acrylamido-2-methylpropanesulphonic acid which is dispersed in the solvent with vigorous stirring. After 30 minutes, the ammonia is added via the upper delivery tube of the flask and the reaction medium is maintained at room temperature for 30 minutes until a pH of about 6–6.5 is obtained. 19.2 g of a 25% solution of trimethylolpropane triacrylate in tert-butanol are then introduced and the reaction medium is heated to 60° C. and simultaneously made inert by introducing nitrogen into the flask. Once this temperature has been reached, dilauroyl peroxide is added. The reaction starts immediately, which is reflected in an increase in temperature and a precipitation of the polymer. 15 minutes after the start of the polymerization, a stream of nitrogen is introduced. 30 minutes after adding the initiator, the temperature of the reaction medium reaches a maximum of 65–70° C. 30 minutes after this temperature has been reached, the medium is heated to reflux and is maintained under these conditions for 2 hours. The formation of a thick paste is observed in the course of the reaction. The mixture is cooled to room temperature and the product obtained is filtered off. The recovered paste is then dried under vacuum at 60–70° C. for 24 hours. 391 g of crosslinked and neutralized poly(2-acrylamido-2-methylpropanesulphonic acid) are obtained, having a viscosity, measured with a Brookfield viscometer, rotor 4, at a spin speed of 100 revolutions/minute in an aqueous 2% solution and at 25° C., of about 7000 cps.

The hydrodynamic radius of the polymer obtained in an aqueous solution, determined by dynamic light scattering, is 160 nm.

EXAMPLE 1
Shampoo

| | |
|---|---|
| Sodium lauryl ether sulphate sold under the name Empicol ESB3/FL by the company Albright and Wilson | 10 g AM |
| Crosslinked poly(2-acrylamido-2-methylpropanesulphonic acid) neutralized with ammonia, prepared according to the process of Preparation Example B, with a viscosity of about 7000 cps in an aqueous 2% solution and at 25° C. | 1.5 g AM |
| Citric acid | 3 g |
| Water pH adjusted to 4.8 (NaOH) qs | 100 g |

This shampoo has the appearance of a thickened clear liquid. It has good foaming properties.

EXAMPLE 2
Shampoo

| | |
|---|---|
| Triethanolamine lauryl ether sulphate | 5 g AM |
| Monoethanolamine lauryl ether sulphate | 5 g AM |
| Crosslinked poly(2-acrylamido-2-methylpropanesulphonic acid) neutralized with ammonia, prepared according to the process of Preparation Example B, with a viscosity of about 7000 cps in an aqueous 2% solution and at 25° C. | 1.0 g AM |
| Hydroxyethylcellulose crosslinked with epichlorohydrin and quaternized with triethanolamine | 0.1 g |
| Water pH adjusted to 7.8 (NaOH) qs | 100 g |

This shampoo has the appearance of a thickened clear liquid. It has good foaming properties.

EXAMPLE 3
Styling gel

| | |
|---|---|
| Vinylpyrrolidone/dimethylaminoethyl methacrylate copolymer sold under the name Copolymer 845 by the company ISP | 1 g AM |
| Crosslinked poly(2-acrylamido-2-methylpropanesulphonic acid) neutralized with ammonia, prepared according to the process of Preparation Example A, with a viscosity of about 15,600 cps in an aqueous 2% solution and at 25° C. | 1.0 g AM |
| 2-Amino-2-methyl-1-propanol (AMP) pH adjusted to 7.5 qs | |
| Absolute ethanol | 8.7 g |
| Fragrance, preserving agent, dye qs | |
| Demineralized water qs | 100 g |

A homogeneous, smooth, clear, thick, stable gel is obtained.

EXAMPLE 4
Clear antisun gel

| | |
|---|---|
| Glycerol | 4 g |
| Crosslinked poly(2-acrylamido-2-methylpropanesulphonic acid) neutralized with ammonia, prepared according to the process of Preparation Example A, with a viscosity of about 16,000 cps in an aqueous 2% solution and at 25° C. | 1.0 g AM |
| Benzene-1,4-bis(3-methylidene-10-camphorsulphonic acid) as an aqueous 33% solution | 6 g |
| Propylene glycol | 18 g |
| Sterilized demineralized water pH = 1.7 | 70 g |

A homogeneous, smooth, clear, thick, stable gel is obtained.

EXAMPLE 5
Clear anti-mosquito gel

| | |
|---|---|
| Glycerol | 4 g |
| Crosslinked poly(2-acrylamido-2-methylpropanesulphonic acid) neutralized with ammonia, prepared according to the process of Preparation Example A, with a viscosity of about 16,000 cps in an aqueous 2% solution and at 25° C. | 0.8 g AM |
| Ethyl N-butyl-N-acetylaminopropionate | 15 g |
| N,N-Diethyl-m-toluamide | 20 g |

-continued

| | |
|---|---|
| Propylene glycol | 18 g |
| 96° Ethanol | 23 g |
| Sterilized demineralized water | 19.2 g |
| pH = 3.95 | |

A homogeneous, smooth, clear, thick, stable gel is obtained.

EXAMPLE 6

Shower gel

| | |
|---|---|
| Crosslinked poly(2-acrylamido-2-methylpropanesulphonic acid) neutralized with ammonia, prepared according to the process of Preparation Example A, with a viscosity of about 16,000 cps in an aqueous 2% solution and at 25° C. | 1.2 g AM |
| Hydrogenated tallow myristyl glycol | 1 g |
| Sodium salt of methyl p-hydroxybenzoate | 0.215 g |
| Disodium salt of ethylenediamine-tetraacetic acid | 0.26 g |
| Glycerol | 4 g |
| 50/50 Dimethyldiallylammonium chloride/acrylamide copolymer as an aqueous 8% solution | 0.5 g |
| 1,3-Dimethylol-5,5-dimethylhydantoin as an aqueous 55% solution | 0.172 g |
| Sodium lauryl ether sulphate containing 2.2 mol of ethylene oxide | 10 g |
| Triethanolamine lauryl sulphate as an aqueous 40% solution | 25 g |
| Cocoylbetaine as an aqueous 32% solution | 5 g |
| Fragrance | 0.15 g |
| NaOH qs pH 7.5 | |
| Sterilized demineralized water qs | 100 g |

A homogeneous, smooth, clear, stable shower gel which has good foaming properties is obtained.

EXAMPLE 7

Shower gel

| | |
|---|---|
| Crosslinked poly(2-acrylamido-2-methylpropanesulphonic acid) neutralized with ammonia, prepared according to the process of Preparation Example B, with a viscosity of about 7000 cps in an aqueous 2% solution and at 25° C. | 1.2 g AM |
| Hydrogenated tallow myristyl glycol | 1 g |
| Sodium salt of methyl p-hydroxybenzoate | 0.215 g |
| Disodium salt of ethylenediamine-tetraacetic acid | 0.26 g |
| Glycerol | 4 g |
| 50/50 Dimethyldiallylammonium chloride/acrylamide copolymer as an aqueous 8% solution | 0.5 g |
| 1,3-Dimethylol-5,5-dimethylhydantoin as an aqueous 55% solution | 0.172 g |
| Sodium lauryl ether sulphate containing 2.2 mol of ethylene oxide | 10 g |
| Triethanolamine lauryl sulphate as an aqueous 40% solution | 25 g |
| Cocoylbetaine as an aqueous 32% solution | 5 g |
| Fragrance | 0.15 g |
| HCl qs pH 5.5 | |
| Sterilized demineralized water qs | 100 g |

A homogeneous, smooth, clear, stable shower gel which has good foaming properties is obtained.

EXAMPLE 8

Mouthwash

| | |
|---|---|
| Crosslinked poly(2-acrylamido-2-methylpropanesulphonic acid) neutralized with ammonia, prepared according to the process of Preparation Example A, with a viscosity of about 16,000 cps in an aqueous 2% solution and at 25° C. | 0.1 g AM |
| Methyl p-hydroxybenzoate | 0.1 g |
| Glycerol | 5 g |
| Sorbitan monolaurate oxyethylenated with 20 mol of ethylene oxide | 0.4 g |
| Sodium lauryl sulphate powder | 0.25 g |
| Sodium fluoride | 0.05 g |
| 96° Ethanol | 5 g |
| Fragrance | 18 g |
| NaOH qs pH 7.5 | |
| Sterilized demineralized water qs | 100 g |

A homogeneous, clear, stable liquid is obtained.

EXAMPLE 9

Mouthwash

| | |
|---|---|
| Crosslinked poly(2-acrylamido-2-methylpropanesulphonic acid) neutralized with ammonia, prepared according to the process of Preparation Example A, with a viscosity of about 16,000 cps in an aqueous 2% solution and at 25° C. | 0.1 g AM |
| Methyl p-hydroxybenzoate | 0.1 g |
| Glycerol | 5 g |
| Sorbitan monolaurate oxyethylenated with 20 mol of ethylene oxide | 0.4 g |
| Sodium lauryl sulphate powder | 0.25 g |
| Sodium fluoride | 0.05 g |
| 96° Ethanol | 5 g |
| Fragrance | 18 g |
| HCl qs pH 5 | |
| Sterilized demineralized water qs | 100 g |

A homogeneous, clear, stable liquid is obtained.

EXAMPLE 10

Refreshing moisturizing gel

| | |
|---|---|
| Crosslinked poly(2-acrylamido-2-methylpropanesulphonic acid) neutralized with ammonia, prepared according to the process of Preparation Example B, with a viscosity of about 7000 cps in an aqueous 2% solution and at 25° C. | 1.5 g AM |
| Glycerol | 3 g |
| 96° Ethyl alcohol in water | 20 g |
| Sterilized demineralized water qs | 100 g |
| pH 4.8 | |

A homogeneous, stable, clear gel is obtained.

EXAMPLE 11
Care cream (oil-in-water emulsion)

| Fatty phase | |
|---|---|
| Sorbitan monostearate containing 20 mol of ethylene oxide | 1 g |
| Glyceryl stearate | 2 g |
| Stearic acid | 1.4 g |
| Triethanolamine | 0.7 g |
| Cetyl alcohol | 0.5 g |
| Sunflower oil | 15 g |
| Cyclomethicone | 5 g |

| Aqueous phase | |
|---|---|
| Crosslinked poly(2-acrylamido-2-methylpropanesulphonic acid) neutralized with ammonia, prepared according to the process of Preparation Example B, with a viscosity of about 7000 cps in an aqueous 2% solution and at 25° C. | 1.2 g AM |
| Glycerol | 5 g |
| Preserving agent | 0.25 g |
| Fragrance | 0.15 g |
| Sterilized demineralized water qs pH 6.5 | 100 g |

A shiny, soft white cream is obtained.

EXAMPLE 12
Moisturizing milk (oil-in-water emulsion)

| Fatty phase | |
|---|---|
| Self-emulsifiable composition sold under the name Montanov 68 by the company Seppic | 2.5 g |
| Jojoba oil | 3 g |
| Corn oil | 13 g |

| Aqueous phase | |
|---|---|
| Crosslinked poly(2-acrylamido-2-methylpropanesulphonic acid) neutralized with ammonia, prepared according to the process of Preparation Example A, with a viscosity of about 16,000 cps in an aqueous 2% solution and at 25° C. | 0.1 g AM |
| Glycerol | 5 g |
| Preserving agent qs | |
| Sterilized demineralized water qs pH 6.0 | 100 g |

This milk is applied easily to the face and to the body and is more particularly soft on application.

EXAMPLE 13
Facial and body cleansing cream (oil-in-water emulsion)

| Fatty phase | |
|---|---|
| Jojoba oil | 20 g |

| Aqueous phase | |
|---|---|
| Crosslinked poly(2-acrylamido-2-methylpropanesulphonic acid) neutralized with ammonia, prepared according to the process of Preparation Example B, with a viscosity of about 7000 cps in an aqueous 2% solution and at 25° C. | 2 g AM |
| Alkyl ($C_8/C_{10}/C_{12}/C_{14}/C_{16}$; 29/37/23/9/2) polyglucoside-1,4 | 6 g |
| Glycerol | 5 g |
| Preserving agent qs | |
| Fragrance | |
| Sterilized demineralized water qs pH 5 | 100 g |

A soft, smooth, shiny and foaming cream is obtained.

EXAMPLE 14
Cream-gel for around the eyes (oil-in-water emulsion)

| Fatty phase | |
|---|---|
| PEG-20 stearate | 1.65 g |
| Cetyl alcohol | 1.05 g |
| Glyceryl stearate | 0.3 g |
| Cyclomethicone | 6 g |

| Aqueous phase | |
|---|---|
| Crosslinked poly(2-acrylamido-2-methylpropanesulphonic acid) neutralized with ammonia, prepared according to the process of Preparation Example B, with a viscosity of about 7000 cps in an aqueous 2% solution and at 25° C. | 1.5 g AM |
| Glycerol | 5 g |
| Preserving agent qs | |
| Distilled water qs pH 5 | 100 g |

A homogeneous, shiny, slightly clear gelled cream is obtained.

EXAMPLE 15
Moisturizing cream (oil-in-water emulsion)

| Fatty phase | |
|---|---|
| Polysorbate 60 | 0.8 g |
| Stearyl alcohol | 1.0 g |
| Glyceryl stearate (AND) PEG100 stearate | 1.0 g |
| Hydrogenated polyisobutene | 10 g |
| Fragrance | 0.3 g |

| Aqueous phase | |
|---|---|
| Crosslinked poly(2-acrylamido-2-methylpropanesulphonic acid) neutralized with ammonia, prepared according to the process of Preparation Example A, with a viscosity of about 16,000 cps in an aqueous 2% solution and at 25° C. | 1.0 g AM |
| Glycerol | 5.0 g |
| Preserving agent qs | |
| Distilled water qs | 100 g |

COMPARATIVE TESTS

The macroscopic appearance of compositions (1) according to the invention, thickened with a crosslinked poly(2-acrylamido-2-methylpropanesulphonic acid) polymer and neutralized with ammonia, prepared according to the process of Preparation Example A, with a viscosity of about 16,000 cps in an aqueous 2% solution and at 25° C., is studied.

These compositions are compared with compositions (2) according to the prior art containing as thickener a non-crosslinked poly(2-acrylamido-2-methylpropanesulphonic acid) polymer such as the commercial product Cosmedia HSP1160 sold by Henkel.

The concentration of thickening polymer is varied in each type of composition, as well as the pH of from 2 to 7.

The compositions of the type (1) and of the type (2) have as formulation:

Composition (1)

| | |
|---|---|
| Crosslinked poly(2-acrylamido-2-methylpropanesulphonic acid) neutralized with ammonia, prepared according to the process of Preparation Example A, with a viscosity of about 16,000 cps in an aqueous 2% solution and at 25° C. | 0.5–2 g AM |
| Distilled water qs pH 2 to 7 | 100 g |

Composition (2)

| | |
|---|---|
| Non-crosslinked poly(2-acrylamido-2-methylpropanesulphonic acid) neutralized with triethanolamine, sold under the name Cosmedia HSP1160 | 0.5–11 g AM |
| Distilled water qs pH 2 to 7 | 100 g |

Relatively thickened, stable, homogeneous, non-sticky and non-stringy gels or creams are obtained with the compositions (1).

Fluid, unstable, heterogeneous, tacky, stringy and sticky gels are obtained with the compositions (2), even at high concentrations of thickening polymer (11% active material).

What is claimed is:

1. A cosmetic or dermatological composition comprising in a cosmetically or dermatological acceptable medium at least one crosslinked, at least 90% neutralized poly(2-acrylamido-2-methylpropanesulphonic acid) polymer.

2. A cosmetic or dermatological composition according to claim 1, wherein said at least one polymer is present as a thickener and/or gelling agent.

3. A cosmetic or dermatological composition according to claim 1, wherein said at least one polymer comprises the following units (a) and (b), distributed randomly:
   (a) at least one unit of formula (I) in an amount ranging from 90 to 99.9% by weight relative to the total weight of said at least one polymer:

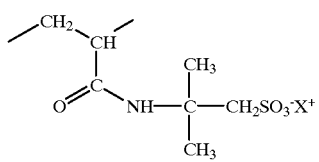

(I)

wherein $X^+$ denotes at least one cation and no more than 10 mol % of said at least one cation $X^+$ comprises protons $H^+$;
   (b) at least one crosslinking unit comprising at least one monomer having at least two olefinic double bonds in an amount ranging from 0.01 to 10% by weight relative to the total weight of said at least one polymer.

4. A cosmetic or dermatological composition according to claim 3, wherein said at least one polymer contains a sufficient number of units of formula to obtain polymer particles whose hydrodynamic volume in solution in water has a radius ranging from 10 to 500 nm, and wherein the distribution of said polymer particles is homogenous and unimodal.

5. A cosmetic or dermatological composition according to claim 3, wherein said at least one unit of formula (I) is present in an amount ranging from 98 to 99.5% by weight, and said at least one crosslinking unit is present in an amount ranging from 0.2 to 2% by weight relative to the total weight of said composition.

6. A cosmetic or dermatological composition according to claim 3, wherein said at least one cation ($X^+$) is a proton, an alkali metal cation, an alkaline-earth metal cation, or an ammonium ion.

7. A cosmetic or dermatological composition according to claim 3, wherein said at least one cation $X^+$ comprises from 90 to 100 mol % $NH_4^+$ cations and from 0 to 10 mol % $H^+$ protons.

8. A cosmetic or dermatological composition according to claim 3, wherein said at least one cross-linking monomer having at least two olefinic double bonds is a monomer of formula (II):

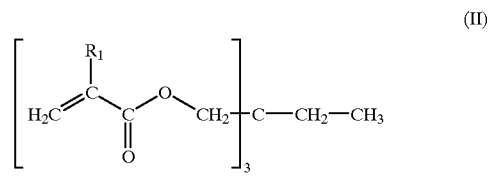

(II)

in which $R_1$ denotes a hydrogen atom or $C_1$–$C_4$ alkyl.

9. A cosmetic or dermatological composition according to claim 8, wherein said at least one cross-linking monomer having at least two olefinic double bonds is methyl (trimethylolpropane triacrylate).

10. A cosmetic or dermatological composition according to claim 1, wherein said at least one polymer has a viscosity, measured with a Brookfield viscometer, rotor 4, at a spin speed of 100 revolutions/minute in an aqueous 2% solution and at 25° C., of at least 1000 cps.

11. A cosmetic or dermatological composition according to claim 10, wherein said at least one polymer has a viscosity ranging from 5000 to 40,000 cps.

12. A cosmetic or dermatological composition according to claim 11, wherein said at least one polymer has a viscosity ranging from 6500 to 35,000 cps.

13. A cosmetic or dermatological composition according to claim 1, wherein said at least one polymer is present in an amount ranging from 0.01 to 20% by weight relative to the total weight of said composition.

14. A cosmetic or dermatological composition according to claim 13, wherein said at least one polymer is present in an amount ranging from 0.1 to 10% by weight relative to the total weight of said composition.

15. A cosmetic or dermatological composition according to claim 1, wherein said composition is in the form of a dispersion, an aqueous or oily gel, a semi-liquid or liquid emulsion, or a suspension or emulsion of soft, semi-solid, or solid consistency.

16. A cosmetic or dermatological composition according to claim 15, wherein said dispersion is a lotion or serum, said liquid or semi-liquid emulsion is an oil-in-water emulsion or a water-in-oil emulsion, and said suspension or emulsion of soft, semi-solid, or solid consistency is in the form of a cream, a paste, a gel, or a solid bar.

17. A cosmetic or dermatological composition according to claim 1, wherein said composition has a pH ranging from 1 to 13.

18. A cosmetic or dermatological composition according to claim 17, wherein said composition has a pH ranging from 2 to 12.

19. A cosmetic or dermatological composition according to claim 1, wherein said medium comprises water or water in combination with at least one cosmetically and/or dermatologically acceptable organic solvent.

20. A cosmetic or dermatological composition according to claim 19, wherein said at least one organic solvent is a hydrophilic organic solvent, a lipophilic organic solvent, or an amphiphilic solvent.

21. A cosmetic or dermatological composition according to claim 19, wherein said at least one organic solvent is present in an amount ranging from 5 to 99% by weight relative to the total weight of said composition.

22. A cosmetic or dermatological composition according to claim 20, wherein said at least one organic solvent is a mono- or polyfunctional alcohol, optionally oxyethylenated polyethylene glycol, propylene glycol ester, sorbitol, a sorbitol derivative, di-alkyl isosorbide, glycol ether, propylene glycol ether or fatty ester.

23. A cosmetic or dermatological composition according to claim 1, wherein said composition further comprises at least one fatty phase.

24. A cosmetic or dermatological composition according to claim 23, wherein said at least one fatty phase is present in an amount ranging from 0 to 50% by weight relative to the total weight of said composition.

25. A cosmetic or dermatological composition according to claim 1, wherein said composition further comprises at least one additive selected from: cosmetic and/or dermatological aqueous or lipophilic gelling agents and/or thickeners; hydrophilic or lipophilic active agents; preserving agents; antioxidants; fragrances; emulsifiers; moisturizers; emollients; sequestering agents; surfactants; polymers; basifying or acidifying agents; fillers; anti-free-radical agents; sunscreens; insect repellants; slimming agents; dyestuffs; bactericides; and antidandruff agents.

26. A cosmetic or dermatological composition according to claim 1, wherein said composition is in the form of a rinse-out or leave-in hair product for washing, care, conditioning, maintenance of style of, or shaping hair.

27. A cosmetic or dermatological composition according to claim 1, wherein said composition is in the form of a care product, a hygiene product, a make-up product, an anti-sun product, or a buccodental care product.

28. A process for thickening or gelling a cosmetic or dermatological composition, said process comprising in a cosmetically or dermatological acceptable medium including at least one crosslinked, at least 90% neutralized, poly (2-acrylamido-2-methylpropanesulphonic acid) polymer in said composition.

29. A process for the non-therapeutic cosmetic treatment of the skin, scalp, hair, eyelashes, eyebrows, nails or mucous membranes, comprising applying at least one composition according to claim 1 to said skin, scalp, hair, eyelashes, eyebrows, nails or mucous membranes.

30. A cosmetic or dermatological composition according to claim 3, wherein said at least one poly(2-acrylamido-2-methylpropane sulphonic acid) polymer is crosslinked with trimethylol propane triacrylate.

* * * * *

UNITED STATES PATENT AND TRADEMARK OFFICE
CERTIFICATE OF CORRECTION

PATENT NO.: 6,120,780

DATED: September 19, 2000

INVENTORS: Christine Dupuis; Isabelle Hansenne; Mireille Maubru; Laurence Sebillotte-Arnaud; Raluca Lorant It is certified that an error appears in the above-identified patent and that said Letters Patent is hereby corrected as shown below:

In claim 4, column 14, line 5, after "formula" insert --(I)--.

Signed and Sealed this

Twenty-fourth Day of April, 2001

Attest:

NICHOLAS P. GODICI

*Attesting Officer*       *Acting Director of the United States Patent and Trademark Office*